(12) United States Patent
Bianchi et al.

(10) Patent No.: US 7,038,093 B2
(45) Date of Patent: May 2, 2006

(54) INTEGRATED PROCESS FOR THE PREPARATION OF PHENOL FROM BENZENE WITH RECYCLING OF THE BY-PRODUCTS

(75) Inventors: Daniele Bianchi, Arese (IT); Rossella Bortolo, Novara (IT); Roberto Buzzoni, San Mauro Torinese (IT); Alberto Cesana, Carate Brianza (IT); Leonardo Dalloro, Bollate (IT); Rino D'Aloisio, Pernate (IT)

(73) Assignee: Polimeri Europa S.p.A., Brindisi (IT)

( * ) Notice: Subject to any disclaimer, the term of this patent is extended or adjusted under 35 U.S.C. 154(b) by 0 days.

(21) Appl. No.: 10/716,460

(22) Filed: Nov. 20, 2003

(65) Prior Publication Data

US 2004/0122264 A1 Jun. 24, 2004

(30) Foreign Application Priority Data

Nov. 28, 2002 (IT) .................... MI2002A2522

(51) Int. Cl.
*C07C 37/00* (2006.01)

(52) U.S. Cl. ...................................... 568/803
(58) Field of Classification Search ................ 568/803
See application file for complete search history.

(56) References Cited

U.S. PATENT DOCUMENTS

| 4,381,973 A | 5/1983 | Jupe et al. |
| 6,133,487 A | 10/2000 | Ungarelli et al. |
| 2004/0077906 A1 | 4/2004 | Dalloro et al. |

FOREIGN PATENT DOCUMENTS

| EP | 0 919 531 | 6/1999 |
| EP | 0 958 861 | 11/1999 |
| WO | WO 03/042146 | 5/2003 |

OTHER PUBLICATIONS

U.S. Appl. No. 10/716,460, filed Nov. 20, 2003, Bianchi et al.
Database Chemabs Online?, AN 1998:560265, XP-002271912, 1998.
Database Chemabs Online?, AN 1956:81894, XP-002271913, 1956.

*Primary Examiner*—Michael L. Shippen
(74) *Attorney, Agent, or Firm*—Oblon, Spivak, McClelland, Maier & Neustadt, P.C.

(57) ABSTRACT

The invention relates to a process for the preparation of phenol comprising the following phases:
1) preparation in continuous of phenol by means of the direct oxidation of benzene with hydrogen peroxide operating with an $H_2O_2$/benzene ratio ranging from 10 to 70%, in a three-phase reaction system comprising a first liquid phase consisting of benzene and an organic solvent, a second liquid phase consisting of water, a solid phase consisting of an activated catalyst based on titanium silicalite TS-1;
2) separation of the phenol and non-reacted benzene from the reaction mixture of the oxidation section (1), by means of fractionated distillation;
3) separation of the solvent and by-products from the mixture coming from the distillation tail (2), by means of basic extraction;
4) transformation of the by-products obtain in section (3) to phenol by means of hydrodeoxygenation with hydrogen operating in continuous, in aqueous solution, at a temperature ranging from 250 to 500° C., at pressures of 1–100 bar and in the presence of a catalyst based on elements of group VIB or their mixtures or group VIII of the periodic table or their mixtures;
5) recycling of the phenol obtained in section (4) to the distillation section (2).

22 Claims, 1 Drawing Sheet

Figure 1:
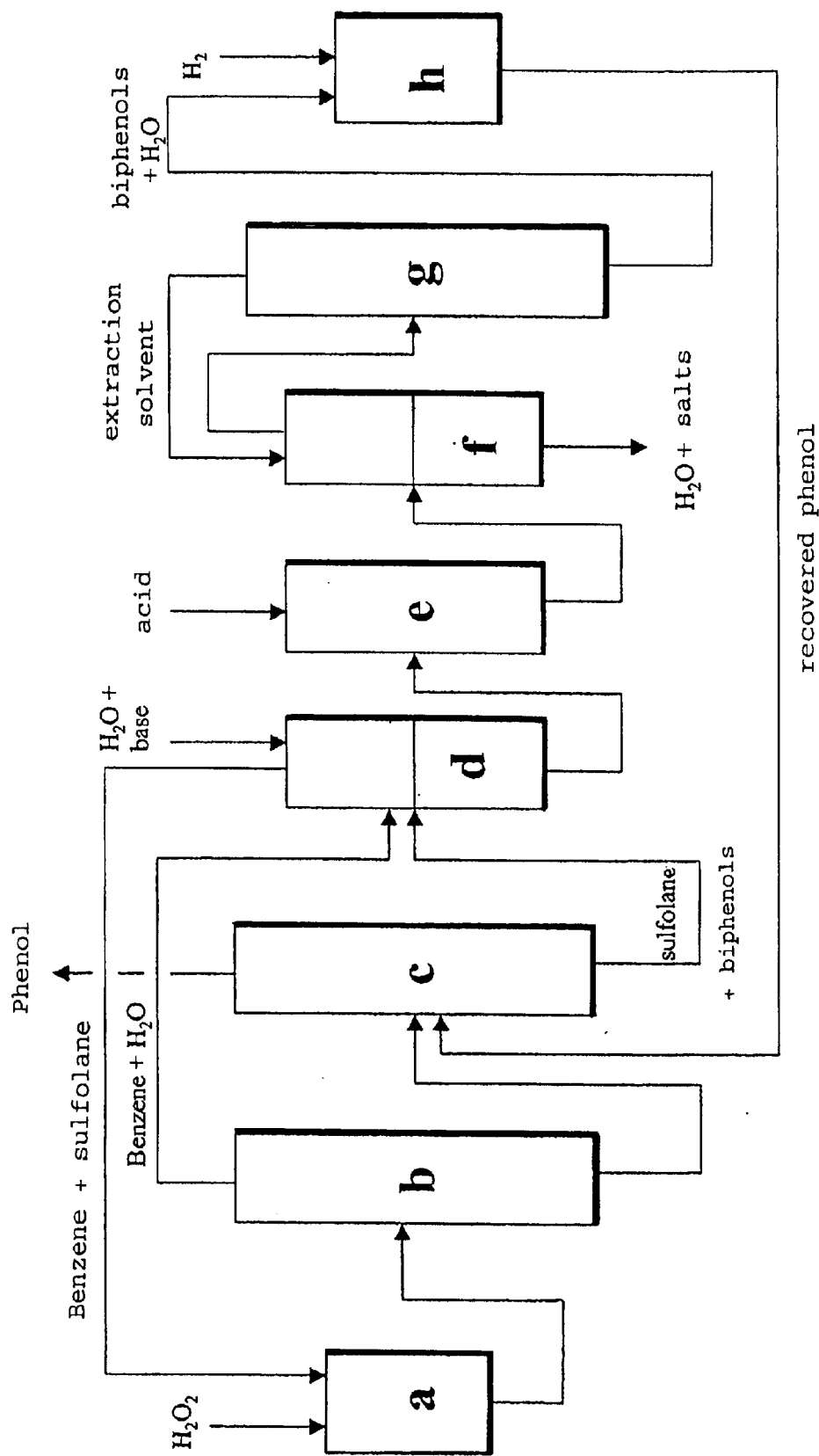

INTEGRATED PROCESS FOR THE PREPARATION OF PHENOL FROM BENZENE WITH RECYCLING OF THE BY-PRODUCTS

The present invention relates to an integrated process for the synthesis of phenol from benzene by the direct oxidation of benzene with hydrogen peroxide, in the presence of a zeolitic catalyst TS-1 and recycling of the by-products.

More specifically, the invention relates to a process for the preparation of phenol wherein the reaction by-products are selectively transformed into phenol and recycled in the process streams.

Phenol is an extremely important industrial intermediate used, for example, in the production of polycarbonates or other phenolic resins.

Phenol is currently produced industrially starting from cumene. Various processes for the preparation of phenol, however, comprising the direct oxidation of benzene with hydrogen peroxide, in the presence of appropriate catalytic systems, are known in the art.

These processes are generally carried out in an organic solvent capable of improving the contact between the organic substrate and hydrogen peroxide such as, for example, methanol, ethanol or isopropyl alcohol. Ketones such as acetone, methylethylketone, or acetic acid or acetonitrile, as described in U.S. Pat. Nos. 4,396,783, GB 2,116,974, are also suitable for the purpose.

European patent application EP A 919531 describes the use of a specific solvent such as sulfolane for obtaining significant improvements in the conversion and selectivity of these processes (EP A 919531). Alternatively, improvements in conversion and selectivity can also be obtained by activation of the catalyst with hydrogen peroxide and fluorine ions, as described in European patent application EP A 958861.

The processes for the preparation of phenol by the direct oxidation of benzene with hydrogen peroxide are generally carried out in a biphasic reaction system (solid catalyst/organic phase), in the presence of suitable catalytic systems.

Italian patent application MI 2001A 002410 describes a process which operates in a three-phase reaction system consisting of a solid catalyst/aqueous phase/organic phase (aromatic compound+solvent) which, with respect to the biphasic system, allows the productivity of the oxidation process of benzene to be increased without jeopardizing the selectivity.

High productivities, however, are not even reached by operating in a three-phase system. This is due to the fact that the process must be carried out at low conversions of benzene to limit the consecutive oxidation reactions of phenol to by-products (catechol and hydroquinone). For example, the above-mentioned patent application MI 2001 A 002410 specifies that with a benzene conversion of 12.2% and a selectivity to phenol of 90%, 111 kg of hydroquinone and catechol (in a 55/45 mixture) are co-produced, for each ton of phenol. The quantity of these by-products is such that they cannot be absorbed by the market and must therefore be disposed of, further increasing the process costs. Furthermore, again as a result of the low productivity, it is necessary to separate and recycle 20.1 kg of solvents (sulfolane, benzene and water) for each Kg of phenol produced. The high volume of recycled products causes an over-dimensioning of the recovery section of the industrial plant.

It has now been found that the drawbacks described above can be reduced when operating according to the process of the present invention.

In practice, the process of the invention envisages integration of the synthesis process of phenol with a hydrodeoxygenation section of the by-products, hydroquinone and catechol, which are selectively transformed into phenol and recycled in the process streams and the running of the synthesis section of phenol under particular operating conditions.

By operating according to the process of the invention, the following advantages are obtained:
 elimination of the co-production of biphenols (the final selectivity to phenol, after recovery of the by-products, proves to be equal to 99%)
 saving in the disposal costs;
 increase in the process productivity, which can be pushed to 159 g of phenol/liter of reaction mixture (as per example 8 of the present patent), with a consequent reduction in the quantity of solvents to be recycled (5.3 kg per kg of phenol) and plant investment costs (relating to the recovery section).

In accordance with this, the object of the present invention relates to a process for the preparation of phenol comprising the following phases:

1) preparation in continuous of phenol by means of the direct oxidation of benzene with hydrogen peroxide operating with an $H_2O_2$/benzene ratio ranging from 10 to 70%, in a three-phase reaction system comprising a first liquid phase consisting of benzene and an organic solvent, a second liquid phase consisting of water, a solid phase consisting of an activated catalyst based on titanium silicalite TS-1;
2) separation of the phenol and non-reacted benzene from the reaction mixture of the oxidation section (1), by means of fractionated distillation;
3) separation of the solvent and by-products from the mixture coming from the distillation tail (2), by means of basic extraction;
4) transformation of the by-products obtained in section (3) to phenol by means of hydrodeoxygenation with hydrogen operating in continuous, in aqueous solution, at a temperature ranging from 250 to 500° C., at pressures of 1–100 bar and in the presence of a catalyst based on elements of group VIB or their mixtures or group VIII of the periodic table or their mixtures;
5) recycling of the phenol obtained in section (4) to the distillation section (2).

The integration between the oxidation process of benzene to phenol and the hydrodeoxygenation of the by-products to phenol is particularly advantageous also because (as described in Italian patent application MI 2002A 001187), it is possible to obtain biphenols, leaving the recovery section of the by-products, in the form of an aqueous solution which can be used directly in the hydrodeoxygenation section without evaporation of the solvent.

Furthermore, the integration of the two processes allows an $H_2O_2$/benzene molar ratio to be adopted within a wider range with respect to the process described in Italian Patent Application MI 2001 A 002410, thus enabling high conversions to benzene and a high productivity to be reached.

Under these conditions, there is a greater formation of by-products which however are converted to phenol in the hydrodeoxygenation section.

The preparation of phenol by the direct oxidation of benzene (FIG. 1, section a) is carried out in a reactor into which benzene, the solvent, water, the catalyst and hydrogen peroxide are fed and where an organic phase is obtained, containing the solvent, non-reacted benzene, water, phenol and by-products (catechol, hydroquinone and phenolic tars).

The three-phase reaction system is reached when operating with a controlled quantity of water which is such as to cause a demixing of the liquid phase and prevent the aggregation of the catalyst.

The oxidation reaction of benzene is conveniently carried out with a concentration of water ranging from 5 to 50% by weight, concentrations ranging from 15 to 40% are preferably used.

The organic solvent can be selected from solvents which are commonly used in the oxidation processes described in the known art such as, for example, methanol, ethanol, isopropyl alcohol, acetone, methylethylketone, acetic acid or acetonitrile.

Particularly preferred for the purposes of the present invention are solvents belonging to the group of sulfones and, among these, sulfolane is preferred, as described in European patent application EP A 919531.

The solvent is used in quantities ranging from 20 to 80% by weight with respect to the reaction mixture.

Quantities ranging from 40 to 70% are preferably used.

The catalysts used in the oxidation reactor of the present invention are selected from those having general formula (I);

$$x\text{TiO}_2 \cdot (1-x)\text{SiO}_2 \qquad (I)$$

wherein: x ranges from 0.0001 to 0.04, preferably from 0.02 to 0.03.

The above titanium silicalites can be prepared according to the method described in U.S. Pat. No. 4,410,501 which also specifies their structural characteristics. The titanium silicalites can also be subjected to activation treatment as described in patent EP A 958861.

Titanium silicalites in which part of the titanium is substituted by other metals such as boron, aluminum, iron or gallium, can also be used.

These substituted titanium silicalites and the methods for their preparation are described in European patent applications 226,257, 226,258 and 266,825.

The catalyst is generally used in quantities ranging from 2 to 60% by weight with respect to the aromatic substrate.

Quantities of catalyst ranging from 5 to 40% by weight with respect to the aromatic substrate are preferably used.

The hydrogen peroxide is added to the reaction mixture in quantities ranging from 10 to 70% in moles with respect to the aromatic substrate, preferably between 20 and 60% in moles.

Solutions of hydrogen peroxide are conveniently used at a concentration ranging from 10 to 60% by weight, preferably from 15 to 60% by weight.

The benzene is normally used in quantities ranging from 10 to 80% by weight with respect to the reaction mixture.

Quantities of benzene ranging from 15 to 50% by weight with respect to the reaction mixture are preferably used.

The oxidation reaction is carried out at temperatures ranging from 500 to 110° C., preferably from 700 to 100° C.

The reaction time necessary for the complete use of the hydrogen peroxide depends on the reaction conditions used.

The oxidation process described in the present invention can be carried out in reactors of the semibatch type (with the feeding of hydrogen peroxide) or of the CSTR type (continuous stirred batch reactor) with feeding in continuous of the hydrogen peroxide and benzene/solvent mixture.

Operating in a continuous process, the aqueous phase (in which the catalyst is selectively distributed), is maintained inside the reactor removing the organic phase in a quiet, unstirred zone in which the demixing is effected. In this way, only one phase containing: an aromatic compound, a solvent, a hydroxy-aromatic compound and by-products, is obtained at the outlet.

By operating under the process conditions of the invention, it is also possible to operate at 100° C. obtaining an increase in the catalytic activity without a loss in selectivity, as normally happened when operating in double phase.

The separation and recovery of the light components of the reaction mixture coming from the oxidation section is carried out by means of fractionated distillation.

The azeotropic mixture of benzene/water is obtained at the head in a first column (FIG. 1, section b) together with a mixture of solvent, phenol and by-products (catechols, hydroquinone, phenolic tars) at the tail. This mixture is sent to a second distillation column (FIG. 1, section c) where purified phenol is obtained at the head and a mixture of solvent and by-products at the tail.

The by-products (catechol, hydroquinone and phenolic tars) are separated from the reaction solvent (preferably sulfolane) by means of the procedure described in Italian patent application MI 2002A 001187, which comprises the following phases:

a mixing and separation section (FIG. 1, section d) fed with the bottom stream of the phenol distillation unit (FIG. 1, section c), consisting of sulfolane and by-products, the benzene stream, coming from the head of the benzene distillation section (FIG. 1, section b) and a basic aqueous solution. An organic phase containing sulfolane, benzene and water (recycled to the section) and an aqueous phase, containing catechol salts, hydroquinone and tars, are obtained at the outlet;

a mixing section (FIG. 1, section e), for the acidification of the aqueous phase coming from section (d) with an inorganic acid or $CO_2$ to release the catechol, hydroquinone and tars from their salts;

a separation section (FIG. 1, section f) fed with the stream coming from section (e) containing water, salts, catechol, hydroquinone and tars, and with an extraction solvent (preferably methylisobutylketone);

a distillation unit section (FIG. 1, section g) for the separation at the head of the extraction solvent which is recycled to section (f) and an aqueous solution of catechol, hydroquinone and tars, at the tail.

The by-products obtained from the recovery section (FIG. 1, section g) are then transformed into phenol by means of hydrodeoxygenation with hydrogen (FIG. 1, section h).

The reaction is carried out in vapour phase at a temperature of 250–500° C., preferably 300–450° C., at a pressure of 1–100 bar, preferably 3–50 bar, and at a space velocity (WHSV=Weight Hourly Space Velocity, expressed in kg of Benzenediols/h/kg of catalyst) of 0.1–10 $h^{-1}$, preferably 0.5–5 $h^{-1}$.

In particular, the feeding of the reactor consists of a solution of benzenediols in water at a concentration of 5–60% by weight, preferably 10–40% by weight, and hydrogen with a molar ratio with respect to the benzenediols of 2–50, preferably 5–30.

The catalyst can be selected from those for hydrodeoxygenation based on elements of group VIB or group VIII of the periodic table.

When the catalyst is based on elements of group VIB, it can contain, as promoters, elements belonging to group VIII and phosphorous. The elements of group VIB can be used in a mixture and, among these, molybdenum and tungsten are preferred. Among the promoters of group VIII, nickel, cobalt, iron and ruthenium are preferred; they can be used in a mixture with each other and with phosphorous.

When the catalyst is based on elements of group VIII, it can contain, as promoters, zinc, rhenium, selenium, tin, germanium and lead. The elements of group VIII can be used in a mixture and, among these, cobalt, palladium, nickel and platinum are preferred. The promoters can also be used in a mixture with each other.

The active phase is preferably deposited on a carrier.

Preferred carriers are inorganic oxides such as alumina, silica, titanium dioxide, crystalline or amorphous aluminosilicates, crystalline spinels having the general formula $F^{2+}R_2^{3+}O_4$ (wherein $F^{2+}$ can be Mg, Fe, Zn, Mn, Ni, etc. and $R^{3+}$ can be Al, Fe, Cr, etc.) or their mixtures.

For catalysts based on an element of group VIB, said element is generally present on the carrier in a concentration ranging from 1 to 50% by weight, preferably from 3–30% by weight. The promoters of these catalysts are generally present in concentrations ranging from 0.1 to 100% atomic with respect to the element of group VIB, preferably from 1 to 50%. Without limiting the possible compositions in any way, or indicating preferences, examples of these catalysts are Mo, W, CoMo, NiMo, NiW, FeMo, RuMo, CoMoP, NiMoP, CoWMo, CoWMoP.

Before being used in the reaction, these catalysts can be subjected to treatment to modify their chemical characteristics, for example sulfuration with $H_2S$, dimethylsulfide, dimethyldisulfide, carbon sulfide or any other compound useful for the purpose.

For catalysts based on an element of group VIII, said element is generally present on the carrier in a concentration ranging from 0.05 to 20% by weight, preferably from 0.1 to 10% by weight. The promoters of these catalysts are generally present in concentrations ranging from 0.5 to 200% atomic with respect to the element of group VIII, preferably from 1 to 120%. Without limiting the possible compositions in any way, or indicating preferences, examples of these catalysts are Pt, Pd, Co, Ni, PtZn, PtRe, PtNi, PtSe, PtSn, PtGe, PtPb, PdPb, PdSn.

With the most appropriate catalysts and operating conditions, it is possible to keep the reactor operating for times prolonged for several hundreds of hours, with a conversion of benzenediols of 100% and a selectivity to phenol >95%.

By prolonging the running of the reactor, the conversion tends to be reduced, whereas the selectivity still remains extremely high. In order to maintain the desired conversion degree, the reaction temperature can be progressively increased within the range of 250–500° C.

It has been verified that the catalysts which can be used for the purposes of the invention can be subjected without any particular problems to periodical regeneration, according to what is known in the state of the art, in order the recover the initial activity.

In particular, the overall process comprises the following sections:

a) oxidation unit, containing the catalyst and fed with benzene, sulfolane, water and hydrogen peroxide;
b) distillation unit for the separation at the head of the water/benzene azeotropic mixture;
c) distillation unit for the separation at the head of the phenol;
d) mixing and separation unit fed with the bottom stream of the distillation unit (c), consisting of sulfolane, biphenols and phenolic tars, the benzene flow, coming from section (b) and a basic aqueous solution. An organic phase is obtained at the outlet, containing sulfolane, benzene and water (recycled to section a) and an aqueous phase, containing salts of biphenols and tars;
e) mixing unit for the acidification of the aqueous phase coming from section (d) with an inorganic acid or $CO_2$ to release the biphenols and tars from their salts;
f) separation unit fed with the stream coming from section (e) containing water, salts, biphenols and tars, and with an extraction solvent (for example methylisobutylketone).
g) distillation unit for the separation at the head of the extraction solvent which is recycled to section (f);
h) hydrodeoxygenation unit containing the catalyst, fed with the stream at the tail of section (g), consisting of biphenols, tars and water, and with hydrogen. The outgoing stream, containing the recovered phenol and water is recycled to section (c).

The simplified integrated process scheme is provided in FIG. 1.

The following examples have the sole purpose of describing the present invention in greater detail and should in no way be considered as limiting its scope.

EXAMPLE 1

Activation of the Catalyst 3.0 g (1.43 mmoles of Ti) of TS-1 catalyst (EniChem, Ti=2.29% by weight) and 0.11 g of $NH_4HF_2$ (average titer 92.5%) in 35 ml of water, corresponding to a molar ratio F/Ti=2.5, are charged into a 100 ml glass flask, equipped with a mechanical stirrer, reflux condenser, thermometer and oil circulation thermostat. The aqueous suspension of the catalyst, maintained under mechanical stirring, is heated to 60° C. 1.6 ml of $H_2O_2$ at 30% by weight, equal to a molar ratio $H_2O_2$/Ti=11, are subsequently added and the suspension is maintained under stirring at 60° C. for 4 hours. After cooling, the solid is separated from the mother liquor (pH 4.3) by filtration on a porous septum, then repeatedly washed with deionized water and finally with acetone. The catalyst is subsequently dried under vacuum at 40° C. for 8 hours and then subjected, with a heating rate of 50° C./h, to thermal treatment in air at 550° C. for 4 hours. Titer of the activated catalyst=1.49% of Ti. The dissolved titanium corresponds to 35% by weight.

EXAMPLE 2

Three-phase system under semi-batch conditions (comparative example MI2001A 002410)

An AISI 316 reactor (volume=600 ml) is pressurized with nitrogen to a pressure of 5 atm. 100 g of benzene (1.28 moles), 180 g of sulfolane, 43 g of water and 10 g of catalyst activated as specified in Example 1 (equal to 3.1 mmoles of Ti) are then charged. The liquid fraction of the reaction mixture is in this case three-phase. The temperature of the reactor is brought to 100° C.

21.75 g (192 mmoles of $H_2O_2$; $H_2O_2$/benzene=0.15) of an aqueous solution of $H_2O_2$ at 30% w/w are subsequently added over a period of 1 hour.

The reaction mixture is then cooled to 20° C. and the catalyst is separated by filtration on a porous septum.

At the end of the reaction two phases are separated, with the following composition:

upper organic phase (85% by weight):
benzene/sulfolane/water 1/3/96 by weight
lower aqueous phase (15% by weight):
benzene/sulfolane/water 61/38/1 by weight.

The organic phase is analyzed by means of HPLC revealing the formation of the following products:

| | |
|---|---|
| phenol | 13.3 g (141.1 mmoles) |
| hydroquinone | 0.69 g (6.3 mmoles) |
| catechol | 1.03 g (9.4 mmoles). |

The reaction mixture was then evaporated at reduced pressure obtaining only traces of polyphenolic tars as boiler residue.

The reaction performances are consequently the following:

benzene conversion (C1)=12.2% (in moles);
$H_2O_2$ conversion (C2)=98% (in moles);
selectivity to phenol (S1)=90% (in moles);
selectivity on $H_2O_2$ (S2)=75% (in moles);
concentration of phenol in the final reaction mixture (organic phase)=4.75% (by weight).

Operating under these conditions, during the recovery and purification phase of the reaction products, it is necessary to evaporate 20.1 Kg of solvent (sulfolane and non-reacted benzene) per Kg of phenol.

The co-production of by-products is equal to 52.0 kg hydroquinone/kg phenol and 78.0 kg catechol/ton phenol.

EXAMPLE 3

An AISI 316 reactor (volume=600 ml) is pressurized with nitrogen to a pressure of 5 atm. 100 g of benzene (1.28 moles), 296 g of sulfolane, 169 g of water and 10 g of catalyst activated as specified in Example 1 (equal to 3.1 mmoles of Ti) are then charged. The liquid fraction of the reaction mixture is in this case three-phase. The temperature of the reactor is brought to 100° C.

29.1 g (257 mmoles of $H_2O_2$; $H_2O_2$/benzene=0.2) of an aqueous solution of $H_2O_2$ at 30% w/w are subsequently added over a period of 1 hour.

The reaction mixture is then cooled to 20° C. and the catalyst is separated by filtration on a porous septum.

At the end of the reaction two phases are separated, with the following composition:

upper organic phase (42% by weight):
benzene/sulfolane/water 56/40/4 by weight
lower aqueous phase (58% by weight):
benzene/sulfolane/water 49/2/49 by weight.

The organic phase is analyzed by means of HPLC revealing the formation of the following products:

| | |
|---|---|
| phenol | 17.5 g (186.5 mmoles) |
| hydroquinone | 1.23 g (11.14 mmoles) |
| catechol | 1.84 g (16.72 mmoles). |

The reaction mixture was then evaporated at reduced pressure obtaining only traces of polyphenolic tars as boiler residue.

The reaction performances are consequently the following:

benzene conversion (C1)=16.7% (in moles);
$H_2O_2$ conversion (C2)=92% (in moles);
selectivity to phenol (S1)=87% (in moles);
selectivity on $H_2O_2$ (S2)=79% (in moles);
concentration of phenol in the final reaction mixture (organic phase)=7.28% (by weight).

Operating under these conditions, during the recovery and purification phase of the reaction products, it is necessary to evaporate 12.7 Kg of solvent (sulfolane and non-reacted benzene) per Kg of phenol.

The co-production of by-products is equal to 69.9 kg hydroquinone/kg phenol and 104.9 kg catechol/ton phenol.

At the end of the separation procedure of the reaction products, described in patent MI 2002A 001187, said by-products are obtained in aqueous solution. The solution, containing catechol (150 g/l) and hydroquinone (100 g/l) is then fed with a flow equal to 0.14 ml/min into a tubular reactor, made of AISI 316 steel, containing 5 g of Angel-hard ESCATT™ H-60 catalyst (Co/Mo/P), at a temperature of 450° C. and a pressure of 25 bar, together with a stream of hydrogen which is such as to maintain a molar ratio hydrogen/(catechol+hydroquinone) equal to 20.5.

Operating under these conditions, a conversion of catechol and hydroquinone equal to 100% is obtained, with a production of 2.49 g (26.5 mmoles) corresponding to a transformation yield to phenol equal to 97%.

The overall selectivity of the process, calculated as total moles of phenol produced/moles of benzene converted×100, proves to be equal to 99%.

EXAMPLE 4

The same procedure is adopted as described in Example 3, adding 21.8 g (384 mmoles of $H_2O_2$; $H_2O_2$/benzene=0.3) of an aqueous solution of $H_2O_2$ at 60% w/w.

The organic phase is analyzed by means of HPLC revealing the formation of the following products:

| | |
|---|---|
| phenol | 23.0 g (245.1 mmoles) |
| hydroquinone | 2.70 g (24.51 mmoles) |
| catechol | 4.04 g (36.77 mmoles). |

The reaction mixture was then evaporated at reduced pressure obtaining only traces of polyphenolic tars as boiler residue.

The reaction performances are consequently the following:

benzene conversion (C1)=23.89% (in moles);
$H_2O_2$ conversion (C2)=98% (in moles);
selectivity to phenol (S1)=80% (in moles);
selectivity on $H_2O_2$ (S2)=65% (in moles);
concentration of phenol in the final reaction mixture (organic phase)=9.85% (by weight).

Under these conditions, during the recovery and purification phase of the reaction products, it is necessary to evaporate 9.2 Kg of solvent (sulfolane and non-reacted benzene) per Kg of phenol.

The co-production of by-products is equal to 117.0 kg hydroquinone/kg phenol and 175.5 kg catechol/ton phenol.

Operating as described in Example 3, the by-products are subject to hydrogenation obtaining a conversion of catechol and hydroquinone equal to 100%, with a production of 5.47 g (58.2 mmoles) corresponding to a transformation yield to phenol equal to 97%.

The overall selectivity of the process, calculated as total moles of phenol produced/moles of benzene converted×100, proves to be equal to 99%.

EXAMPLE 5

The same procedure is adopted as described in Example 3, adding 29.1 g (513 mmoles of $H_2O_2$; $H_2O_2$/benzene=0.4) of an aqueous solution of $H_2O_2$ at 60% w/w.

The organic phase is analyzed by means of HPLC revealing the formation of the following products:

| | |
|---|---|
| phenol | 27.4 g (291.63 mmoles) |
| hydroquinone | 3.83 g (34.84 mmoles) |
| catechol | 5.75 g (52.27 mmoles). |

The reaction mixture was then evaporated at reduced pressure obtaining only traces of polyphenolic tars as boiler residue.

The reaction performances are consequently the following:

benzene conversion (C1)=29.53% (in moles);
$H_2O_2$ conversion (C2)=98% (in moles);
selectivity to phenol (S1)=77% (in moles);
selectivity on $H_2O_2$ (S2)=58% (in moles);
concentration of phenol in the final reaction mixture (organic phase)=11.73% (by weight).

Operating under these conditions, during the recovery and purification phase of the reaction products, it is necessary to evaporate 7.5 Kg of solvent (sulfolane and non-reacted benzene) per Kg of phenol.

The co-production of by-products is equal to 139.8 kg hydroquinone/kg phenol and 209.7 kg catechol/ton phenol.

Operating as described in Example 3, the by-products are subject to hydrogenation obtaining a conversion of catechol and hydroquinone equal to 100%, with a production of 7.78 g (82.7 mmoles) corresponding to a transformation yield to phenol equal to 97%.

The overall selectivity of the process, calculated as total moles of phenol produced/moles of benzene converted×100, proves to be equal to 99%.

EXAMPLE 6

An AISI 316 reactor (volume=600 ml) is pressurized with nitrogen to a pressure of 5 atm. 100 g of benzene (1.28 moles), 216 g of sulfolane, 85 g of water and 10 g of catalyst activated as specified in Example 1 (equal to 3.1 mmoles of Ti) are then charged. The liquid fraction of the reaction mixture is in this case three-phase. The temperature of the reactor is brought to 100° C.

29.1 g (257 mmoles of $H_2O_2$; $H_2O_2$/benzene=0.2) of an aqueous solution of $H_2O_2$ at 30% w/w are subsequently added over a period of 1 hour.

The reaction mixture is then cooled to 20° C. and the catalyst is separated by filtration on a porous septum.

At the end of the reaction two phases are separated, with the following composition:

upper organic phase (43% by weight):
benzene/sulfolane/water 55/41/4 by weight
lower aqueous phase (57% by weight):
benzene/sulfolane/water 49/2/49 by weight.

The organic phase is analyzed by means of HPLC revealing the formation of the following products:

| | |
|---|---|
| phenol | 17.5 g (186.5 mmoles) |
| hydroquinone | 1.33 g (12.11 mmoles) |
| catechol | 2.00 g (18.17 mmoles). |

The reaction mixture was then evaporated at reduced pressure obtaining only traces of polyphenolic tars as boiler residue.

The reaction performances are consequently the following:

benzene conversion (C1)=16.9% (in moles);
$H_2O_2$ conversion (C2)=98% (in moles);
selectivity to phenol (S1)=86% (in moles);
selectivity on $H_2O_2$ (S2)=74% (in moles);
concentration of phenol in the final reaction mixture (organic phase)=9.93% (by weight).

Operating under these conditions, during the recovery and purification phase of the reaction products, it is necessary to evaporate 9.1 Kg of solvent (sulfolane and non-reacted benzene) per Kg of phenol.

The co-production of by-products is equal to 76.2 kg hydroquinone/kg phenol and 114.3 kg catechol/ton phenol.

Operating as described in Example 3, the by-products are subject to hydrogenation obtaining a conversion of catechol and hydroquinone equal to 100% is obtained, with a production of 2.70 g (28.8 mmoles) corresponding to a transformation yield to phenol equal to 97%.

The overall selectivity of the process, calculated as total moles of phenol produced/moles of benzene converted×100, proves to be equal to 99%.

EXAMPLE 7

The same procedure is adopted as described in Example 6, adding 21.8 g (384 mmoles of $H_2O_2$; $H_2O_2$/benzene=0.3) of an aqueous solution of $H_2O_2$ at 60% w/w.

The organic phase is analyzed by means of HPLC revealing the formation of the following products:

| | |
|---|---|
| phenol | 22.69 g (241.4 mmoles) |
| hydroquinone | 2.65 g (24.14 mmoles) |
| catechol | 3.98 g (36.20 mmoles). |

The reaction mixture was then evaporated at reduced pressure obtaining only traces of polyphenolic tars as boiler residue.

The reaction performances are consequently the following:

benzene conversion (C1)=23.5% (in moles);
$H_2O_2$ conversion (C2)=98% (in moles);
selectivity to phenol (S1)=80% (in moles);
selectivity on $H_2O_2$ (S2)=64% (in moles);
concentration of phenol in the final reaction mixture (organic phase)=13.41% (by weight).

Operating under these conditions, during the recovery and purification phase of the reaction products, it is necessary to evaporate 6.5 Kg of solvent (sulfolane and non-reacted benzene) per Kg of phenol. reacted benzene) per Kg of phenol.

The co-production of by-products is equal to 117.0 kg hydroquinone/kg phenol and 175.5 kg catechol/ton phenol.

Operating as described in Example 3, the by-products are subject to hydrogenation obtaining a conversion of catechol and hydroquinone equal to 100%, with a production of 5.38 g (57.3 mmoles) corresponding to a transformation yield to phenol equal to 97%.

The overall selectivity of the process, calculated as total moles of phenol produced/moles of benzene converted×100, proves to be equal to 99%.

EXAMPLE 8

The same procedure is adopted as described in Example 6, adding 29.1 g (513 mmoles of $H_2O_2$; $H_2O_2$/benzene=0.4) of an aqueous solution of $H_2O_2$ at 60% w/w.

The organic phase is analyzed by means of HPLC revealing the formation of the following products:

| | |
|---|---|
| phenol | 26.9 g (286.6 mmoles) |
| hydroquinone | 3.98 g (36.20 mmoles) |
| catechol | 5.97 g (54.30 mmoles). |

The reaction mixture was then evaporated at reduced pressure obtaining only traces of polyphenolic tars as boiler residue.

The reaction performances are consequently the following:

benzene conversion (C1)=29.4% (in moles);
$H_2O_2$ conversion (C2)=98% (in moles);
selectivity to phenol (S1)=76% (in moles);
selectivity on $H_2O_2$ (S2)=57% (in moles);
concentration of phenol in the final reaction mixture (organic phase)=15.95% (by weight).

Operating under these conditions, during the recovery and purification phase of the reaction products, it is necessary to evaporate 5.3 Kg of solvent (sulfolane and non-reacted benzene) per Kg of phenol.

The co-production of by-products is equal to 147.8 kg hydroquinone/kg phenol and 221.7 kg catechol/ton phenol.

Operating as described in Example 3, the by-products are subject to hydrogenation obtaining a conversion of catechol and hydroquinone equal to 100%, with a production of 8.08 g (85.9 mmoles) corresponding to a transformation yield to phenol equal to 97%.

The overall selectivity of the process, calculated as total moles of phenol produced/moles of benzene converted×100, proves to be equal to 99%.

What is claimed is:

1. A process for the preparation of phenol comprising the following phases:
   1) continuously preparing phenol by means of the direct oxidation of benzene with hydrogen peroxide operating with an $H_2O_2$/benzene ratio ranging from 10 to 70%, in a three-phase reaction system comprising a first liquid phase consisting of benzene and an organic solvent, a second liquid phase consisting of water, a solid phase consisting of an activated catalyst based on titanium silicalite TS-1;
   2) separating the phenol and non-reacted benzene from the reaction mixture of the oxidation section (1), by means of fractionated distillation;
   3) separating the solvent and by-products consisting of benzenediols from the mixture coming from the distillation tail (2), by means of basic extraction;
   4) transforming the by-products obtained in section (3) to phenol by means of hydrodeoxygenation with hydrogen operating in continuous, in aqueous solution, at a temperature ranging from 250 to 500° C., at pressures of 1–100 bar and in the presence of a catalyst based on elements of group VIB or their mixtures or group VIII of the periodic table or their mixtures;
   5) recycling of the phenol obtained in section (4) to the distillation section (2).

2. The process according to claim 1, wherein the direct oxidation of benzene occurs in a three-phase reaction system comprising a quantity of water ranging from 5 to 50% by weight with respect to the reaction mixture.

3. The process according to claim 2, wherein the water is present in a quantity ranging from 15 to 40%.

4. The process according to claim 1, wherein the direct oxidation of benzene occurs in a three-phase reaction system comprising an organic solvent consisting of sulfolane, in quantities ranging from 20 to 80% by weight with respect to the reaction mixture.

5. The process according to claim 4, wherein the sulfolane is present in quantities ranging from 40 to 70%.

6. The process according to claim 1, wherein the direct oxidation of benzene with hydrogen peroxide is carried out in the presence of a catalyst based on titanium silicalite TS-1 selected from those having general formula (I);

$$xTiO_2.(1-x)SiO_2 \qquad (I)$$

wherein: x ranges from 0.0001 to 0.04, in an amount that ranging from 2 to 60% by weight with respect to the benzene, activated by means of a pretreatment with fluorine ions and hydrogen peroxide.

7. The process according to claim 6, wherein the catalyst is present in an amount ranging from 5 to 40% by weight with respect to the benzene.

8. The process according to claim 1, wherein the direct oxidation occurs in an amount of benzene ranging from 10 to 80% by weight with respect to the reaction mixture.

9. The process according to claim 8, wherein the direct oxidation occurs in an amount of benzene ranging from 15 to 50% by weight with respect to the reaction mixture.

10. The process according to claim 1, wherein the oxidation reaction occurs at temperatures ranging from 50° to 110° C.

11. The process according to claim 10, wherein the oxidation reaction is carried out at temperatures ranging from 70° to 100° C.

12. The process according to claim 1, wherein the by-products consisting of benzenediols which are transformed into phenol are in aqueous solution at a concentration of 5–60% by weight.

13. The process according to claim 12, wherein the benzenediols are in aqueous solution at a concentration of 10–40% by weight.

14. The process according to claim 1, wherein the hydrodeoxygenation is effected with hydrogen operating with a molar ratio with respect to the benzenediols of 2–50.

15. The process according to claim 14, wherein the molar ratio ranges from 5–30.

16. The process according to claim 1, wherein the hydrode-oxygenation occurs in the presence of a catalyst based on elements of group VIB and a promoter selected from elements belonging to group VIII and phosphorous.

17. The process according to claim 16, wherein the catalyst based on elements of group VIB is selected from molybdenum and tungsten and the promoter is selected from nickel, cobalt, iron and ruthenium.

18. The process according to claim 1, wherein the hydrode-oxygenation occurs in the presence of a catalyst based on elements of group VIII selected from cobalt, palladium, nickel and platinum and a promoter selected from zinc, rhenium, selenium, tin, germanium and lead.

19. The process according to claim 1, wherein the hydrode-oxygenation occurs in the presence of a catalyst deposited on a carrier.

20. The process according to claim 19, wherein the carrier is selected from alumina, silica, titanium dioxide, crystalline or amorphous alumino-silicates, crystalline spinels having the general formula $F^{2+}R_2^{3+}O_4$, wherein $F^{2+}$ is selected from Mg, Fe, Zn, Mn, Ni, and $R^{3+}$ is selected from Al, Fe, Cr or their mixtures.

21. The process according to claim 16 and 19, wherein the hydrodeoxygenation is carried out in the presence of a catalyst based on an element of group VIB deposited on a carrier at a concentration ranging from 1 to 50% by weight and a promoter at a concentration ranging from 0.1 to 100% atomic with respect to the element of group VIB.

22. The process according to claim 18 and 19, wherein the hydrodeoxygenation is carried out in the presence of a catalyst based on an element of group VIII deposited on a carrier at a concentration ranging from 0.05 to 20% by weight and a promoter at a concentration ranging from 0.5 to 200% atomic with respect to the element of group VIII.

* * * * *